PROCESS FOR PROCESSING SILVER HALIDE DEVELOPING AGENTS

BACKGROUND OF THE INVENTION

1. Field of the Invention

This invention relates to a process for producing ligand developers of the following formula:

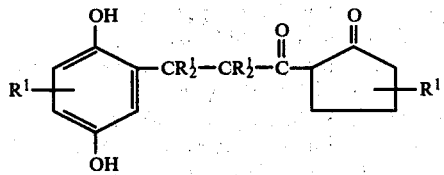

FORMULA 1 where, each $R^1$ can be the same or different substituent chosen from those that will not impair the functionality of the compound as a silver halide developing agent but preferably, each $R^1$ is hydrogen.

2. Description of the Prior Art

Compounds of Formula 1 are known and have been described in at least the following U.S. Patents: U.S. Pat. Nos. 3,629,336; 3,772,368, 3,789,062; 3,812,191 and 3,903,169.

U.S. Pat. Nos. 3,772,368; 3,813,192 and 3,903,169 are particularly directed to methods for producing compounds of Formula 1. For example, U.S. Pat. No. 3,772,368 relates to a method involving reacting a Schiff base anion with a lactone to provide compounds of Formula 1 while U.S. Pat. No. 3,903,169 discloses a method for producing compounds of Formula 1 by way of a condensation reaction between a cyclopentanone anion and a lactone.

The method disclosed in U.S. Pat. No. 3,812,191 is somewhat different from the methods of the patents discussed above involving as it does, the preparation of a compound of the following formula:

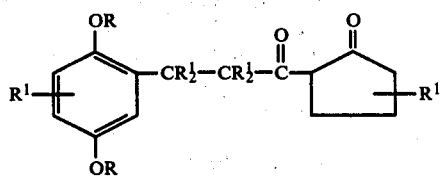

FORMULA 2 where, $R^1$ is as defined before and each R provides a protecting function and is a substituent which can be removed by hydrolysis to provide the compound of Formula 1. Specifically, the method of U.S. Pat. No. 3,812,191 involves the preparation of a "protected" compound of Formula 2 e.g., the compound [3-(2,5-decathyloxyphenyl) propionyl] -2-cyclopentanone and the removal of the protecting groups — the cathyloxy groups—to provide a compound of Formula 1.

According to the method disclosed in referenced U.S. Pat. No. 3,812,191, the cathyloxy groups of the [3-(2,5-dicathyloxyphenyl) propionyl] -2-cyclopentanone are removed by saponifying the protected compound in a substantially non-aqueous, solubilizing medium comprising a solution of an alkali metal hydroxide in an alcohol and acidifying the saponified product to a pH of between about 6.0 to about 7.0 and preferably between about 6.5 to about 7.0. The controlled acidification of the saponified product is an important factor in the method of U.S. Pat. No. 3,812,191 leading to commercially acceptable yields of compounds of Formula 1. For example, if the saponified product is acidified to a pH below 6.0 and particularly to a pH below 3.0, the predominant product is not the compound of Formula 1 but rather a cyclized compound of the following formula:

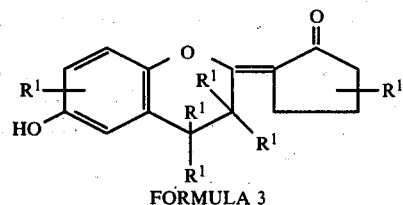

FORMULA 3

In accordance with the practice of the present invention it has been found that the cyclized compounds of Formula 3 are valuable intermediates in the production of developer ligands of Formula 1 since the cyclized compounds can be easily opened up by hydration to provide the compound of Formula 1.

BRIEF SUMMARY OF THE INVENTION

Essentially the process of the present invention involves the following general hydration reaction:

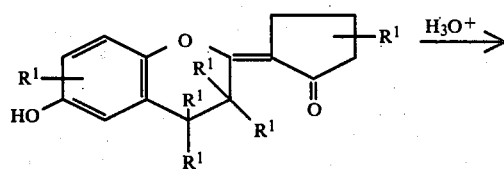

FORMULA 3

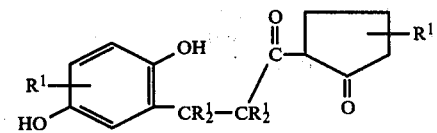

FORMULA 1

According to this invention, cyclized compounds of Formula 3 are hydrated or "opened up" by reacting the cyclized compound with acids in aqueous or partially aqueous media. However, in the particularly preferred embodiment of this invention, the cyclized compounds are hydrated using specific acids in combination with specific reaction solvents or media.

The particularly preferred acids used in the process of this invention are acids of moderate strength having pKa values between about 1.0 and 3.0. Weaker acids such as acetic acid (pKa 4.75) have been found to be extremely slow in "opening up" compounds of Formula 3. Also, the stronger acids such as hydrochloric, sulfuric or trifluoroacetic acid appear to cause degradation of compounds of Formula 3 and provide poor yields of compounds of Formula 1. In accordance with this invention, the particularly preferred acids are organic acids such as chloroacetic acid (pKa 2.85) or dichloroacetic acid (pKa 1.48) but inorganic acids having pKa values between about 1.0 to about 3.0 can also be suitably employed. The amount of acid(s) used is not espe-

2-METHYL-3-NITROBENZOPHENONE

This is a division of application Ser. No. 736,663 filed Oct. 29, 1976, now U.S. Pat. No. 4,065,477.

This invention pertains to a process for the preparation of 1-nitroanthraquinone and to a novel intermediate suitable for the preparation thereof. More particularly, this invention pertains to a process for preparing 1-nitroanthraquinone from 3-nitro-o-xylene via the novel intermediate 2-methyl-3-nitrobenzophenone.

The compound 1-nitroanthraquinone, and its reduction product 1-aminoanthraquinone, are important intermediates in the preparation of pigments, vat dyes, disperse dyes and acid dyes. Currently, 1-aminoanthraquinone is manufactured by either nitrating anthraquinone and reducing the nitration product, or sulfonating anthraquinone and aminating the sulfonation product.

The product obtained by the nitration process is accompanied by 2-nitroanthraquinone and 1,5-, 1,8-, 1,6-, and 1,7-dinitroanthraquinone, undesirable contaminants. In order to obtain high quality 1-aminoanthraquinone from this product, multiple purification steps are required after the nitration and reduction reactions.

The product obtained by the sulfonation process is contaminated by a mercury salt catalyst which is required in order to specifically sulfonate the 1-position of anthraquinone. All of the mercury salt catalyst must be recovered and reused to satisfy ecological and economic requirements. There is a need therefore for a process for the production of high purity 1-nitroanthraquinone which can be reduced to high purity 1-aminoanthraquinone.

I have discovered a novel process for the preparation of 1-nitroanthraquinone which comprises partially oxidizing 3-nitro-o-xylene (I) to 2-methyl-3-nitrobenzoic acid (II); converting II to the 2-methyl-3-nitrobenzoylhalide (III); converting III to the novel intermediate 2-methyl-3-nitrobenzophenone (IV); oxidizing IV to 2-benzoyl-6-nitrobenzoic acid (V), and cyclizing V to 1-nitroanthraquinone (VI), as shown in chart I.

CHART I

In theory one could partially oxidize 3-nitro-o-xylene to 2-methyl-6-nitrobenzoic acid (VII), convert VII to a 2-methyl-6-nitrobenzoyl halide (VIII), convert VIII to 2-methyl-6-nitrobenzophenone (IX), oxidize IX to 2-benzoyl-3-nitrobenzoic acid (X) and cyclize the latter to 1-nitroanthraquinone. However, the conversion of VIII to IX is accompanied by side reactions which produce a black resinous unidentifiable product. Therefore, the preparation of 1-nitroanthraquinone (VI) by this route, as outlined in Chart II below, is not feasible.

CHART II

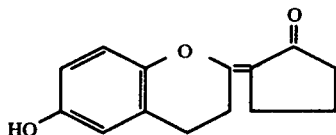

in a medium comprising a mixture of water and an organic miscible solvent where the water in said medium comprises from about 30% to about 60% by volume of the total volume of water and solvent, and an acid having a pKa between about 1.0 and about 3.0 in an amount sufficient to provide at least about 1 mole equivalent of acid per mole of cyclized compound to provide a compound of the Formula:

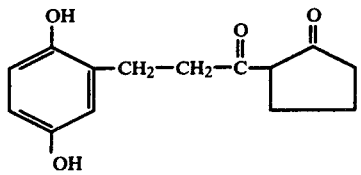

6. A process of claim 5 where said acid is chosen from the group consisting of chloroacetic acid, dichloroacetic acid and mixtures thereof.

7. A process of claim 5 where said miscible organic solvent is chosen from the group consisting of methanol, ethanol, isopropanol, acetone and mixtures of these.

8. A process of claim 5 where the water in said medium comprises about 50% by volume of the total volume of water and solvent.

9. A process which comprises the step of hydrating a cyclized compound of the Formula:

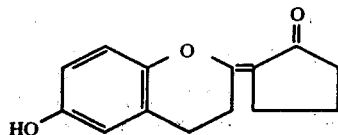

in a medium comprising a mixture of water and a water miscible organic solvent where the amount of water is between about 30% and about 60% by volume of total volume of the water and solvent chosen from the group consisting of methanol, ethanol, isopropanol, acetone and mixtures of these and an acid selected from the group consisting of chloroacetic acid, dichloroacetic acid or mixtures thereof in an amount sufficient to provide at least about 1 mole equivalent of acid per mole of cyclized compound to provide a compound of the Formula:

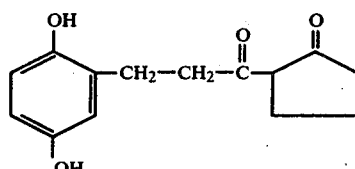

10. A process of claim 9 where the water in said medium comprises about 50% by volume of the total volume of water and solvent.

11. A process of claim 9 where said acid is chloroacetic acid.

12. A process of claim 9 where said acid is dichloroacetic acid.

* * * * * with 200 mls. of benzene. The benzene layer was separated and combined with the organic phase and the combined solution was washed successively with water, a dilute aqueous solution of sodium carbonate, and water. The organic phase was dried over anhydrous sodium sulfate, filtered, concentrated and distilled to obtain 2-methyl-3-nitrobenzophenone (11.45 grams; 95% yield; b.p. 183° C. at 2 mm; m.p. 42° C. after recrystallization from Calculated for $C_{14}H_{11}NO_3$ (percent by weight): C, 69.70; H, 4.59; N, 5.8 Found: C, 69.50; H, 4.62; N, 5.54

(D) Preparation of 2-Benzoyl-6-Nitrobenzoic Acid

A mixture of 2-methyl-3-nitrobenzophenone (24.1 grams; 0.10 mole) and a 19.2% aqueous solution of nitric acid, prepared by adding 20 mls. of concentrated nitric acid to 75 mls. of water and mixing thoroughly, was stirred in a sealed autoclave at 150° C. for a period of 24 hours. The autoclave was then cooled to room temperature, vented and the contents discharged. The reaction mixture was extracted with 350 mls. of chloroform and the chloroform extract was separated from the aqueous phase and concentrated to a volume of 150 mls. The chloroform concentrate was washed with a dilute aqueous solution of sodium carbonate and the aqueous layer was separated and acidified by adding dilute hydrochloric acid thereto. The resulting slurry was allowed to stand at room temperature for several hours and the solid was separated by filtration and dried. The product 2-benzoyl-6-nitrobenzoic acid (14.1 grams; 52% yield) was identified by comparison of its infrared spectrum with that of an authentic sample.

(E) Preparation of 1-Nitroanthraquinone

A solution of 2-benzoyl-6-nitrobenzoic acid (2.0 grams; 0.0074 mole) in 10 mls. of concentrated sulfuric acid (99.5% by weight) was stirred at 100° C. for 3 hours, then cooled to room temperature and poured into a mixture of ice and water. The resulting mixture was filtered to recover the precipitated solids. The filter cake was then washed successively with a dilute aqueous solution of sodium carbonate and water, and dried to obtain 1-nitroanthraquinone (1.59 grams; 85% yield). The product was identified by comparison of its vapor phase chromatographic spectrum with that of an authentic sample.

I claim:

1. The compound having the structural formula:

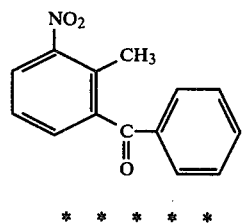

* * * * *